(12) United States Patent
Amidi

(10) Patent No.: US 7,688,198 B2
(45) Date of Patent: Mar. 30, 2010

(54) APPARATUS AND METHOD FOR MONITORING HAZARDOUS MATERIALS IN A PROCESSING OR OTHER ENVIRONMENT

(75) Inventor: Soroush Amidi, Montreal (CA)

(73) Assignee: Honeywell International Inc., Morristown, NJ (US)

( * ) Notice: Subject to any disclaimer, the term of this patent is extended or adjusted under 35 U.S.C. 154(b) by 396 days.

(21) Appl. No.: 11/606,834

(22) Filed: Nov. 29, 2006

(65) Prior Publication Data

US 2008/0122641 A1 May 29, 2008

(51) Int. Cl.
*G08B 1/08* (2006.01)

(52) U.S. Cl. .......................... 340/539.13; 340/539.22; 340/539.26

(58) Field of Classification Search ......... 340/632–634, 340/540, 539.22–539.27, 539.1–539.13; 588/401–415, 249; 702/22–32
See application file for complete search history.

(56) References Cited

U.S. PATENT DOCUMENTS

| | | | | |
|---|---|---|---|---|
| 5,917,433 A * | 6/1999 | Keillor et al. | ............... | 340/989 |
| 5,926,103 A * | 7/1999 | Petite | .................... | 340/825.19 |
| 6,116,815 A * | 9/2000 | Chen | ........................... | 405/52 |
| 6,415,646 B1 * | 7/2002 | Kessel et al. | ................... | 73/23.2 |
| 6,529,137 B1 * | 3/2003 | Roe | ........................ | 340/691.1 |
| 6,891,476 B2 * | 5/2005 | Kitaguchi et al. | ........ | 340/573.1 |
| 7,191,097 B1 * | 3/2007 | Lee et al. | .................... | 702/183 |
| 7,380,210 B2 * | 5/2008 | Lontka et al. | ............... | 715/705 |
| 7,397,381 B2 * | 7/2008 | DiPiazza | .................. | 340/573.1 |
| 2003/0052792 A1 * | 3/2003 | Koyano et al. | .............. | 340/632 |
| 2003/0114986 A1 | 6/2003 | Padmanabhan et al. | | |
| 2003/0214397 A1 | 11/2003 | Perkins et al. | | |
| 2004/0119591 A1 | 6/2004 | Peeters | | |
| 2004/0145485 A1 * | 7/2004 | Tice | ........................... | 340/632 |
| 2006/0176169 A1 | 8/2006 | Doolin et al. | | |

FOREIGN PATENT DOCUMENTS

| | | |
|---|---|---|
| DE | 10331909 A1 | 1/2005 |
| EP | 1 657 610 A2 | 5/2006 |
| WO | WO 2006/026953 A1 | 3/2006 |

OTHER PUBLICATIONS

"IntelaTrac PKS Redefines Field Data Collection and Management," Honeywell, Feb. 2006, 2 pages.

(Continued)

*Primary Examiner*—Benjamin C Lee
*Assistant Examiner*—Michael Shannon
(74) *Attorney, Agent, or Firm*—Munck Carter, LLP

(57) ABSTRACT

A sensor detects one or more hazardous materials, such as by measuring the concentration of one or more hazardous gasses. The sensor or an external system can also determine a location of the sensor. This location can be associated with the measured data from the sensor at the external system or at the sensor. The location could be determined at the sensor using GPS or RFID. The location could be determined at the external system using RFID. The external system can use the measured data and the location information to perform a wide variety of tasks, such as mapping hazardous materials in a processing or other environment or identifying trends in the concentration of the hazardous materials.

20 Claims, 5 Drawing Sheets

OTHER PUBLICATIONS

Honeywell Process Solutions, "IntelaTrac PKS," Honeywell, 2 pages, Feb. 2008.
Honeywell Process Solutions, "IntelaTrac PKS," Honeywell, 2 pages, Feb. 2008.
"Improve Maintenance Efforts with DocuMint," Honeywell, Feb. 2006, 2 pages.
"Lumidor Minimax XT," Honeywell, Dec. 2005, 4 pages.
"PanOS Platform, Unified Location Management Platform," PanGo, 2007, 2 pages.
"Ekahau T301-A Wi-Fi Tag," ekahau, 2007, 2 pages.

* cited by examiner

APPARATUS AND METHOD FOR MONITORING HAZARDOUS MATERIALS IN A PROCESSING OR OTHER ENVIRONMENT

TECHNICAL FIELD

This disclosure relates generally to portable devices and more specifically to an apparatus and method for monitoring hazardous materials in a processing or other environment.

BACKGROUND

Many different processing environments have to deal with the presence of noxious, harmful, or other hazardous materials. For example, chemical production facilities often use or produce hazardous gasses or other chemicals. As another example, coal mines and other types of mines often have hazardous gasses that build up within the mines. In these or other environments, it is often necessary or desirable to allow personnel to determine the level of hazardous materials in these environments.

To satisfy this need, personnel often carry hazardous material sensors, such as hazardous gas sensors. These hazardous material sensors typically determine the concentrations of hazardous materials in the immediate vicinity of the sensors. If the measured concentrations exceed a threshold, an alarm is typically sounded to warn the personnel of the excessive hazardous material concentrations.

SUMMARY

This disclosure provides an apparatus and method for monitoring hazardous materials in a processing or other environment.

In a first embodiment, an apparatus includes a sensor operable to detect one or more hazardous materials. The apparatus also includes a tracking system operable to at least one of: identify a location of the apparatus and initiate transmission of a signal for identifying the location of the apparatus. The apparatus further includes an interface operable to transmit data from the sensor, where the data is associated with the detection of the one or more hazardous materials.

In particular embodiments, the sensor is operable to measure a concentration of the one or more hazardous materials, and the tracking system is operable to determine the location of the apparatus. The interface is operable to transmit one or more measured concentrations and one or more determined locations.

In other particular embodiments, the tracking system is operable to initiate transmission of signals used by an external system to identify the location of the apparatus.

In a second embodiment, a method includes detecting one or more hazardous materials at a portable sensor. The method also includes identifying a location of the portable sensor at the portable sensor. The method further includes transmitting data associated with the detection of the one or more hazardous materials and the identified location of the sensor to an external system.

In a third embodiment, a computer program is embodied on a computer readable medium and is operable to be executed by a processor. The computer program includes computer readable program code for receiving measurement data associated with one or more hazardous materials from a sensor, where the sensor is associated with an environment. The computer program also includes computer readable program code for at least one of: receiving location data identifying a location of the sensor and determining location data identifying the location of the sensor. In addition, the computer program includes computer readable program code for analyzing the measurement data and the location data to determine at least one characteristic of the environment.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
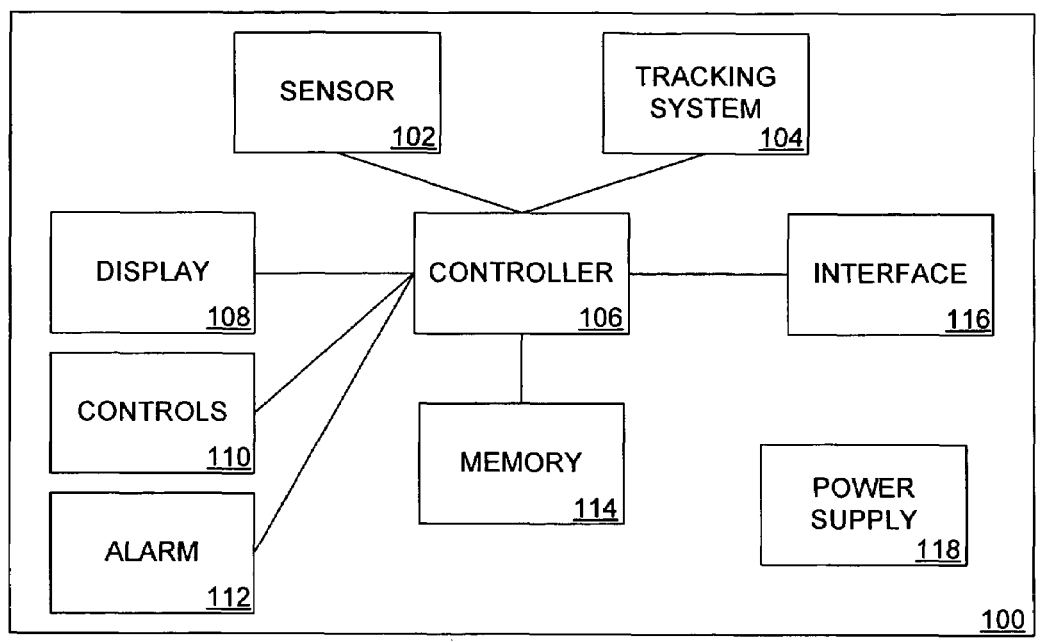
FIG. 1 illustrates an example hazardous material sensor according to one embodiment of this disclosure.

FIG. 1 illustrates an example hazardous material sensor 100 according to one embodiment of this disclosure. The embodiment of the hazardous material sensor 100 shown in FIG. 1 is for illustration only. Other embodiments of the hazardous material sensor 100 may be used without departing from the scope of this disclosure.

In this example, the hazardous material sensor 100 collects readings associated with one or more hazardous materials, such as by measuring the concentration of one or more hazardous gasses in the vicinity of the hazardous material sensor 100. The hazardous material sensor 100 can also be used to provide location information to an external system, such as by identifying any locations where the measured concentration of a hazardous gas exceeds a specified threshold. In this way, the hazardous material sensor 100 allows personnel (such as production plant or mine operators) to perform various functions (such as mapping the locations of hazardous materials or determining the movement or trend of hazardous materials in a processing or other environment).

In this example, the hazardous material sensor 100 includes at least one sensor 102. The sensor 102 detects the presence of one or more hazardous materials around the hazardous material sensor 100. The sensor 102 could also measure the amount of one or more hazardous materials around the hazardous material sensor 100, such as by determining the concentration of one or more hazardous gasses in the local atmosphere. The one or more hazardous materials could represent any type of material or materials that are harmful to people or to equipment or other objects. As examples, the hazardous materials could include caustic chemicals and dangerous gasses (such as carbon monoxide, hydrogen sulphide, or even oxygen). The sensor 102 includes any suitable structure capable of detecting the presence of and possibly measuring the amount of one or more hazardous materials in an environment.

The hazardous material sensor 100 also includes a tracking system 104. The tracking system 104 allows the hazardous material sensor 100 or an external system to identify the location of the hazardous material sensor 100. This may allow, for example, the external system to identify any locations where hazardous material concentrations exceed a threshold. The tracking system 104 may use any suitable technique to identify the location of the hazardous material sensor 100. As examples, the tracking system 104 could represent a Global Positioning System (GPS) receiver capable of identifying a location of the hazardous material sensor 100 using the GPS satellite system. The tracking system 104 could also represent a Radio Frequency Identification (RFID) system that communicates with external RFID components. In these embodiments, the tracking system 104 could receive signals identifying the current location of the hazardous material sensor 100. The tracking system 104 could also initiate transmission of signals (such as beacon signals) that are used by an external system to identify the location of the hazardous material sensor 100. These signals could be initiated by the tracking system 104 in any suitable manner, such as at a specified interval or in response to receiving paging signals. The tracking system 104 may use any suitable communication scheme, such as GPS, Ultra Wide Band, active or passive RFID, low power Wireless Fidelity (WIFI), or any other wireless communication technology. The tracking system 104 includes any suitable structure facilitating identification of the location of the hazardous material sensor 100, whether the identification occurs within or outside of the hazardous material sensor 100.

A controller 106 is coupled to the sensor 102 and optionally the tracking system 104. The controller 106 performs various functions related to the operation of the hazardous material sensor 100. For example, the controller 106 could receive measurement data from the sensor 102 and present the measurement data to a user on a display 108. The controller 106 could also receive input from the user through one or more controls 110, where the input alters or controls the operation of the hazardous material sensor 100. The controller 106 could further trigger one or more alarms 112 when the measurement data from the sensor 102 indicates that a hazardous material concentration exceeds a threshold or that the presence of a hazardous material has been detected (meaning the threshold is zero). In addition, the controller 106 could assist the tracking system 104 in identifying the location of the hazardous material sensor 100, such as by analyzing signals received by the tracking system 104. The controller 106 includes any hardware, software, firmware, or combination thereof for performing various operations in the hazardous material sensor 100. The controller 106 could, for example, represent a microprocessor, digital signal processor, application specific integrated circuit (ASIC), or field programmable gate array (FPGA).

The display 108 includes any suitable structure for presenting information to a user, such as a liquid crystal display (LCD). The controls 110 include any suitable structure(s) allowing the user to control or adjust the operation of the hazardous material sensor 100, such as a button initiating the measurement of a hazardous material. The alarms 112 include any suitable structure(s) providing a warning of one or more conditions to the user. The alarms 112 could include multiple types of alarms, such as a light emitting diode (LED) creating a visual indicator, a speaker creating an audible indicator, and a vibrator creating a tactile indicator. Moreover, different types of visual, audible, and tactile indicators could be used, such as when one set of indicators is used when a measured hazardous material concentration exceeds a lower threshold and another set of indicators is used when the measured concentration exceeds a higher threshold.

The hazardous material sensor 100 may also include a memory 114. The memory 114 stores various information used or collected by the hazardous material sensor 100. For example, the memory 114 could include one or more memories storing instructions and data used by the controller 106 to perform various functions, such as a computer program executed by the controller 106. In some embodiments, the controller 106 stores (i) hazardous material measurements from the sensor 102 and/or (ii) location information from the tracking system 104 in the memory 114. In these embodiments, this information can later be transmitted or downloaded from the hazardous material sensor 100 to an external system, such as a process control system controlling operation of various devices and systems in a processing or other environment. In other embodiments, the controller 106 does not store the hazardous material measurements from the sensor 102 or the location information from the tracking system 104. In these embodiments, depending on the implementation, the memory 114 could be omitted from the hazardous material sensor 100.

The hazardous material sensor 100 may further include an interface 116. The interface 116 allows the hazardous material sensor 100 to communicate and exchange information with an external system. For example, the interface 116 may allow the controller 106 to transmit measurement data and location information stored in the memory 114 to the external system. This could occur wirelessly or via a physical connection, such as when the hazardous material sensor 100 is inserted into a docking station. The interface 116 represents any suitable interface supporting wired or wireless communications.

In addition, the hazardous material sensor 100 includes a power supply 118. The power supply 118 supplies power to various components in the hazardous material sensor 100. The power supply 118 could represent any suitable source of operating power, such as a 3.6V non-replaceable Lithium battery or other non-replaceable or replaceable battery. In some embodiments, the power supply 118 may be capable of supplying power to the hazardous material sensor 100 for an extended period of time, such as two years or more.

In one aspect of operation, the hazardous material sensor 100 could represent a portable device, such as a device worn or carried by personnel in a processing or other environment (like in a production plant or mine). The sensor 102 collects various readings of one or more hazardous materials in the processing or other environment. These readings can be displayed to the user, and they could be transmitted to an external system or stored for later communication to the external system. The tracking system 104 performs actions for identifying the location of the hazardous material sensor 100. For example, the tracking system 104 could broadcast a beacon signal. The transmission of a beacon from the tracking system 104 could be accompanied by measurement data from the sensor 102, allowing the external system to identify the location of the hazardous material sensor 100 and the measurement data taken at that location. The tracking system 104 could also collect location information transmitted by beacons in the processing or other environment or otherwise determine the location of the hazardous material sensor 100. The controller 106 could associate measurement data with the identified location and transmit the information to the external system in real-time or store the information in the memory 114 for later retrieval. Other configurations or modes of operation of the hazardous material sensor 100 could also be used depending on the implementation.

In this way, the external system can receive (either in real-time or non-real-time) hazardous material sensor measurements and location information. This allows the external system to perform various functions. For example, the external system could map the locations of hazardous materials in the processing or other environment. The external system could also determine how hazardous materials move in the processing or other environment, detect a build-up of hazardous materials, or detect trends in the presence of hazardous materials. The external system could identify any other characteristic(s) of the processing or other environment using this data.

Any suitable threshold or thresholds could be used in the hazardous material sensor 100. For example, the hazardous material sensor 100 may be capable of detecting carbon monoxide, hydrogen sulphide, and oxygen levels. Example thresholds for these materials are provided in Table 1 below.

TABLE 1

| Hazardous Material | Lower Threshold | Upper Threshold |
| --- | --- | --- |
| Carbon Monoxide | 35 PPM | 100 PPM |
| Hydrogen Sulphide | 10 PPM | 15 PPM |
| Oxygen | 23.5% | 19.5% |

Although FIG. 1 illustrates one example of a hazardous material sensor 100, various changes may be made to FIG. 1. For example, the hazardous material sensor 100 could include any number of each individual component, such as multiple displays or memories. Also, the functional division shown in FIG. 1 is for illustration only. Various components in FIG. 1 could be combined or omitted and additional components could be added according to particular needs. As a particular example, the tracking system 104 and interface 116 could be combined into a single wireless system for transmitting measurement and location data and transmitting or receiving beacon signals. As another particular example, the controller 106 could form part of or be integrated with the tracking system 104 and perform various functions related to the identification of the hazardous material sensor's location.

Figure 2:
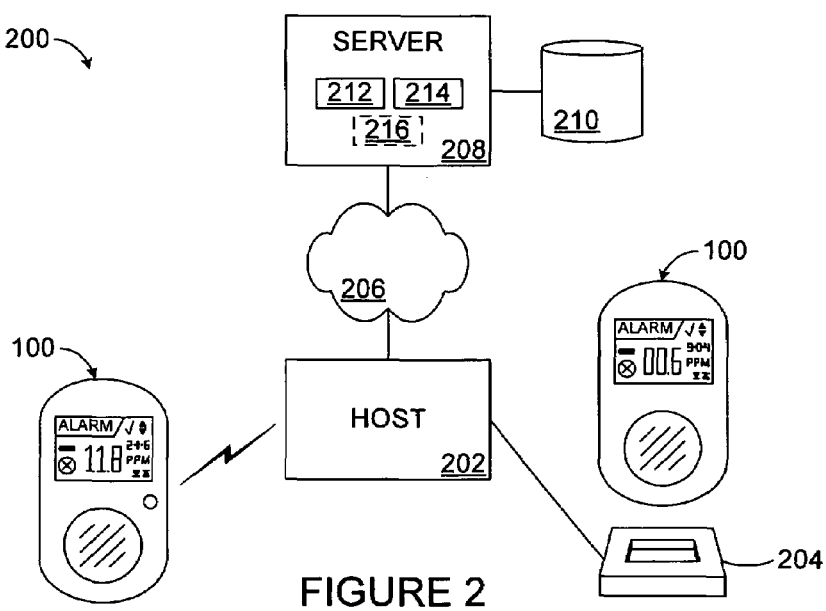
FIGS. 2 and 3 illustrate example systems for collecting measurements from hazardous material sensors according to one embodiment of this disclosure.
Figure 3:
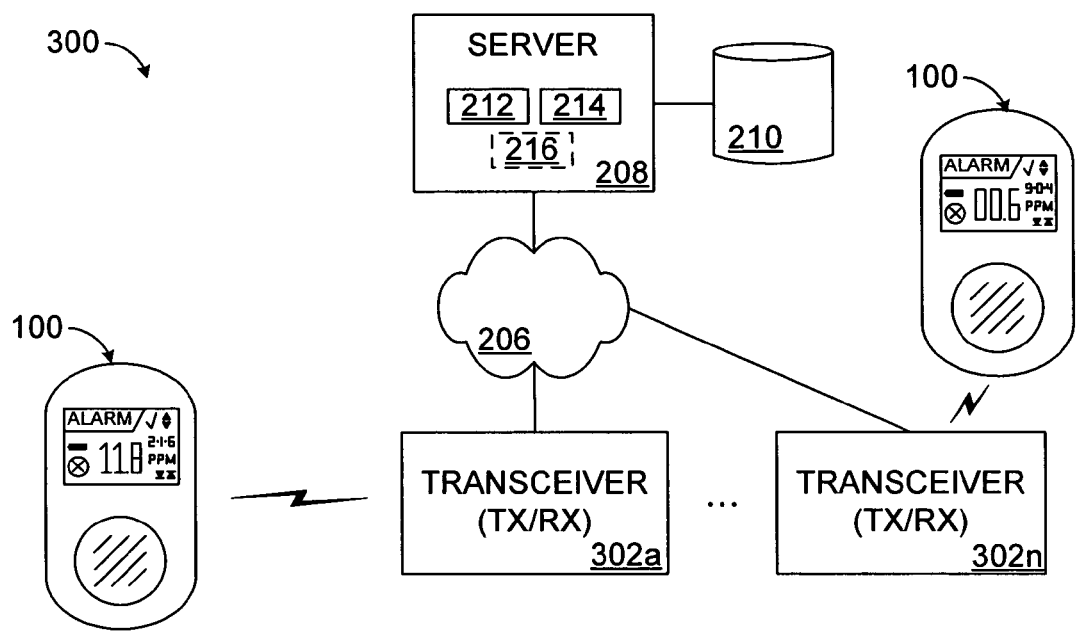

FIGS. 2 and 3 illustrate example systems for collecting measurements from hazardous material sensors according to one embodiment of this disclosure. The embodiments of the systems shown in FIGS. 2 and 3 are for illustration only. Other embodiments of each system may be used without departing from the scope of this disclosure.

As shown in FIG. 2, a system 200 collects data from one or more hazardous material sensors 100. In this example, the hazardous material sensors 100 are encased in generally oval-shaped housings. The housings could be waterproof, weather resistant, and impact resistant and include alligator clips or other mechanisms for attached to personnel. The hazardous material sensors 100 could, however, also be attached to moveable objects such as conveyor belts, vehicles, or other objects. Each hazardous material sensor 100 includes a display presenting various information to a user, a button for initiating a hazardous material measurement, and a speaker for presenting an audible alarm.

As shown in this example, the display on each hazardous material sensor 100 includes the current reading made by the sensor 102. The unit of measurement for the reading is presented to the right of the displayed reading, which could include parts per million ("PPM") or percent ("%"). The value above the unit of measurement identifies the remaining lifetime of the hazardous material sensor 100. This may represent the estimated remaining lifetime of the power supply 118 or any other suitable value. In this example, the lifetimes are shown in month-week-day format, meaning one hazardous material sensor 100 has two months, one week, and six days remaining while the other has nine months, zero weeks, and four days remaining. A battery symbol indicates whether the power supply 118 is running low.

A checkmark in the upper right corner of the display indicates that the reading is acceptable or it does not exceed a threshold. A circled "X" in the bottom left corner indicates that the reading is not acceptable or it exceeds the threshold. The arrows in the top right corner indicate whether the measured reading exceeds a lower threshold or an upper threshold. For example, when no arrow is present but an alarm is activated, the lower threshold for one or more hazardous gasses may have been exceeded. When the upper arrow is displayed, this means that at least one hazardous material (such as carbon dioxide or hydrogen sulphide) has exceeded its upper threshold. When the bottom arrow is displayed, this means that at least one other hazardous material (such as oxygen) has exceeded its upper threshold. The arrows in the bottom right corner indicate whether the current reading is the high peak or low peak of the sensor's recent readings.

In this example, the hazardous material sensors 100 can be used to store hazardous material measurements and locations that are then downloaded to a host 202. The host 202 could represent any suitable device for receiving data from the hazardous material sensors 100, such as a desktop computer, laptop computer, or other computing device. The host 202 may communicate in any suitable manner with the hazardous material sensors 100, such as through a docking station 204 or other wired or wireless connection.

The data collected by the host 202 can be transported over a network 206 to a server 208, which may store the data in a database 210. The network 206 facilitates communication between various components in the system 200. For example, the network 206 may communicate Internet Protocol (IP) packets, frame relay frames, Asynchronous Transfer Mode (ATM) cells, or other suitable information between network addresses. The network 206 may include one or more local area networks (LANs), metropolitan area networks (MANs), wide area networks (WANs), all or a portion of a global network such as the Internet, or any other communication system or systems at one or more locations.

The server 208 may represent any suitable device for storing and using measurement data collected by the hazardous material sensors 100 and location data. In this example, the server 208 includes one or more processors 212 and one or more memories 214 capable of storing data and instructions used by the processors 212. As a particular example, the server 208 could include one or more applications 216 executed by the processor(s) 212. The applications 216 could use the data from the hazardous material sensors 100 to perform a wide variety of functions. For example, an application 216 could map the locations of excessive hazardous materials in a processing or other environment, determine how hazardous materials move, detect a build-up of hazardous materials, or detect trends in the presence or concentration of hazardous materials. The application 216 could perform any other or additional functions using the data from the hazardous material sensors 100.

The database 210 represents any hardware, software, firmware, or combination thereof capable of storing and facilitating retrieval of information. The database 210 may also use any of a variety of data structures, arrangements, and compilations to store and facilitate retrieval of information. While shown as residing outside of and being coupled directly to the server 208, the database 210 could reside in any location or locations accessible by the server 208.

As shown in FIG. 3, a system 300 includes the network 206, server 208, and database 210 described above with respect to FIG. 2. In this example, the hazardous material sensors 100 communicate with one or more transceivers 302a-302n. The transceivers 302a-302n could be distributed across a processing or other environment and used to communicate with the hazardous material sensors 100. The transceivers 302a-302n include any suitable structure for transmitting information to or receiving information from the hazardous material sensors 100. The transceivers 302a-302n could, for example, represent radio frequency (RF) transmitters and receivers.

In some embodiments, the transceivers 302a-302n detect beacon signals or other signals from the hazardous material sensors 100. The transceivers 302a-302n may also receive measurement data from the hazardous material sensors 100, either as part of or separate from the beacon or other signals. In this way, a transceiver 302a-302n, server 208, or other device in the system 300 can associate measurement data from a hazardous material sensor 100 with location information (based on which transceiver receives the data from the hazardous material sensor 100).

In other embodiments, the transceivers 302a-302n transmit beacon signals or other signals to the hazardous material sensors 100. The hazardous material sensors 100 associate these signals with measurement data to associate a location with the measurement data. The hazardous material sensors 100 may then communicate this data to the server 208, either via the transceivers 302a-302n or via the host 202.

In still other embodiments, the transceivers 302a-302n are not used to identify the locations of the hazardous material sensors 100. Rather, the hazardous material sensors 100 may be capable of determining their own positions, such as by using GPS. In these embodiments, the transceivers 302a-302n could be used to receive measurement and location data from the hazardous material sensors 100 for communication to the server 208.

Although FIGS. 2 and 3 illustrate examples of systems for collecting measurements from hazardous material sensors 100, various changes may be made to FIGS. 2 and 3. For example, the layout and arrangement of the systems could vary, and any number of hosts, networks, transceivers, servers, and databases could be used. Also, components could be combined or omitted and additional components could be added according to particular needs. Further, the transceivers 302a-302n could be replaced by transmitters or receivers based on the configuration and operation of the hazardous material sensors 100. Beyond that, the hazardous material sensors 100 could be used in any other suitable system. In addition, a combination of the systems 200 and 300 could be used, such as when data is transmitted to the server 208 through the transceivers 302a-302n and through the host 202.

Figure 4:
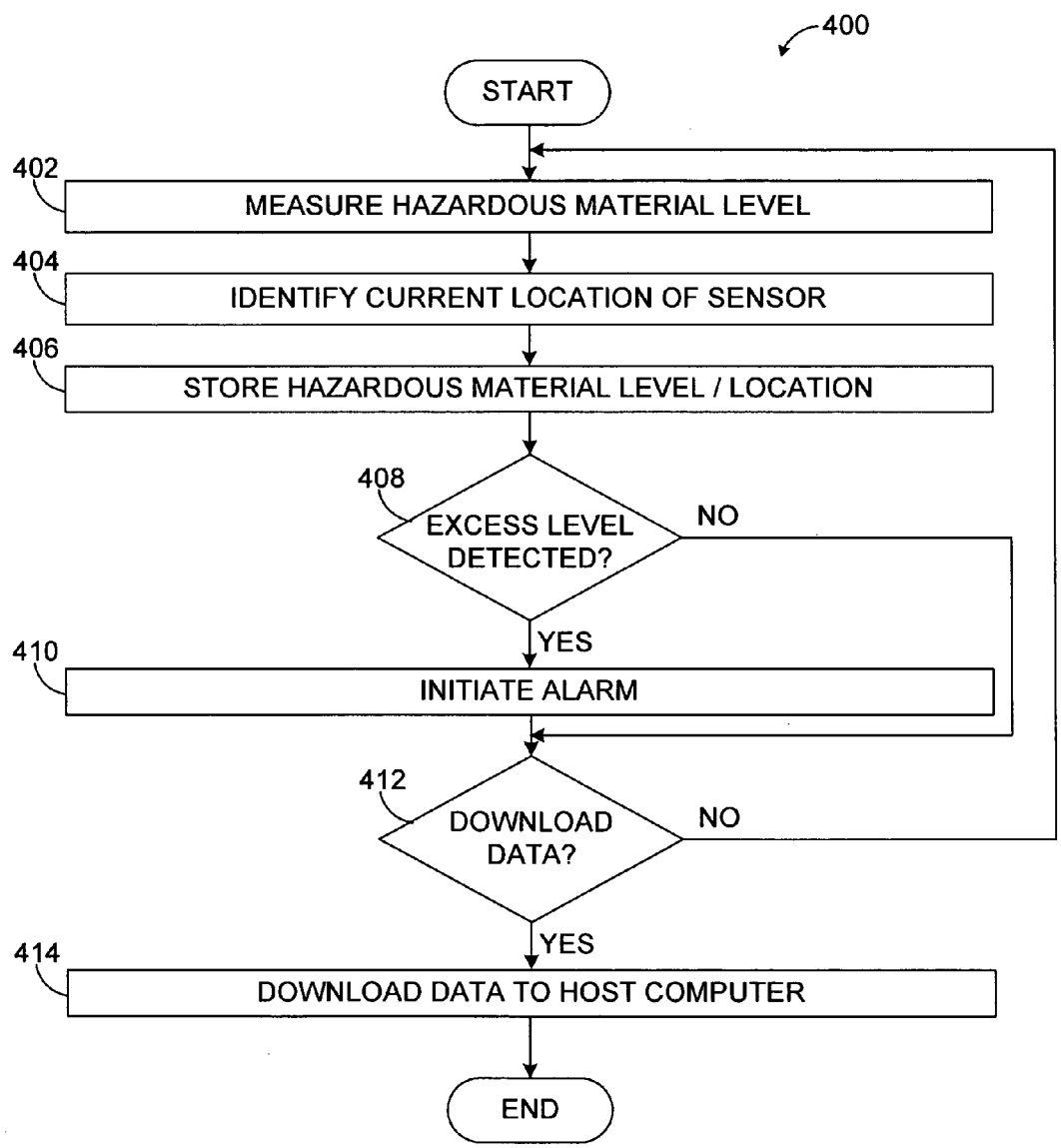
FIGS. 4 and 5 illustrate example methods for collecting measurements at a hazardous material sensor according to one embodiment of this disclosure.
Figure 5:
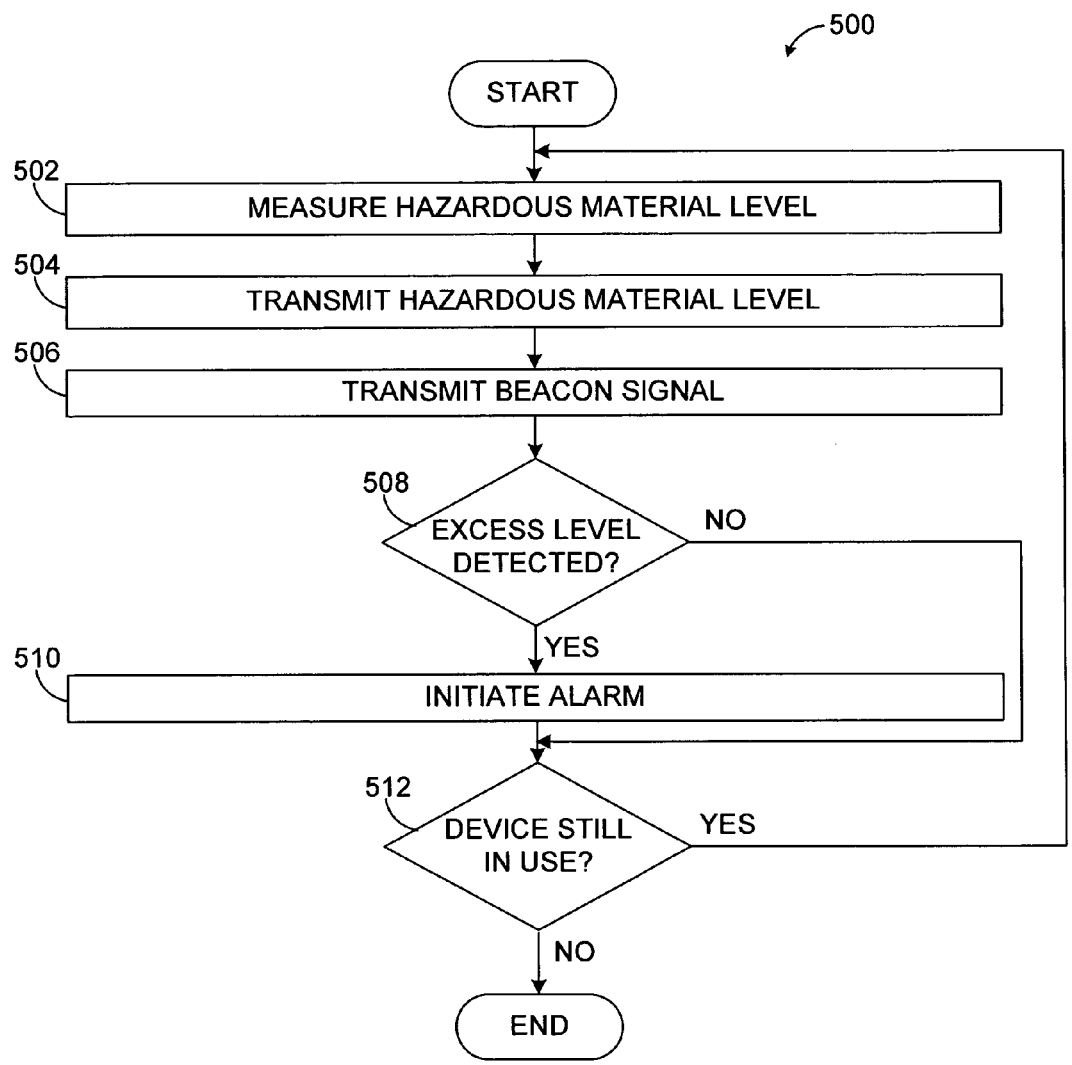

FIGS. 4 and 5 illustrate example methods for collecting measurements at a hazardous material sensor according to one embodiment of this disclosure. The embodiments of the methods shown in FIGS. 4 and 5 are for illustration only. Other embodiments of each method may be used without departing from the scope of this disclosure. Also, for ease of explanation, the methods in FIGS. 4 and 5 are described with respect to the hazardous material sensor 100 of FIG. 1 operating in the systems of FIGS. 2 and 3. The methods could be used with any other suitable device and in any other suitable system.

As shown in FIG. 4, a method 400 includes measuring a level of one or more hazardous materials at step 402. This could include the sensor 102 in the hazardous material sensor 100 measuring the concentration of one or more hazardous gasses. This could also include determining whether a hazardous material is present in any quantity.

A current location of the hazardous material sensor 100 is determined at step 404. The current location could be a precise location or a general location, such as a specified portion of a facility or section of a cave. The current location could be determined in any suitable manner, such as by using GPS or receiving beacon signals from one or more of the RF transceivers 302a-302n.

The hazardous material measurement and current location are stored at step 406. This could include the controller 106 storing the hazardous material measurement and current location in the memory 114 of the hazardous material sensor 100.

If the measured hazardous material level is excessive at step 408, at least one alarm is initiated at step 410. This could include the controller 106 determining if the measured concentration of a hazardous gas exceeds either a lower threshold or an upper threshold. If so, the visual, audible, or tactile alarm appropriate for the exceeded threshold can be initiated.

Otherwise, if it is not time to download the collected data at step 412, the method returns to step 402 to collect additional data. Otherwise, the collected data is downloaded to a host at step 414. This could include the controller 106 communicating the collected data from the memory 114 to the host 202 via the interface 116. The communication could involve wired or wireless communications.

As shown in FIG. 5, a method 500 includes measuring a level of one or more hazardous materials at step 502. The measured level is then communicated to an external system at step 504. This could include the controller 106 in the hazardous material sensor 100 communicating the measurement to a transceiver 302a-302n via the interface 116.

A beacon signal is also transmitted at step 506. The beacon signal could, for example, be transmitted by the tracking system 104 to enable at least one of the transceivers 302a-302n to detect the signal. In this way, the location of the hazardous material sensor 100 can be determined by the external system. While shown as separate transmissions, steps 504-506 could be combined and involve the transmission of a single signal used to carry measurement data and identify the location of the hazardous material sensor 100.

If the measured hazardous material level is excessive at step 508, at least one alarm is initiated at step 510. Otherwise, if the hazardous material sensor 100 remains in use at step 512, the method returns to step 502 to collect additional data. Otherwise, no additional data is collected, and the method ends.

Although FIGS. 4 and 5 illustrate examples of methods for collecting measurements at a hazardous material sensor 100, various changes may be made to FIGS. 4 and 5. For example, while shown as a series of steps, each method could include steps that overlap or that occur in parallel. Also, various ones of the steps in FIGS. 4 and 5 could be reordered. Further, while shown as storing or transmitting each individual measurement (and possibly the corresponding location), this data could be stored or transmitted only after an excessive measurement has been detected. Beyond that, the specific mechanism in each method for determining location is for illustration only. Each method could involve any suitable technique for determining the location of a hazardous material sensor 100, whether that technique is performed by the external system or the hazardous material sensor 100. In addition, a combination of the methods 400 and 500 could be used, such as when data is transmitted in real-time and also stored for later downloading (to ensure no data is lost during real-time transmission).

Figure 6:
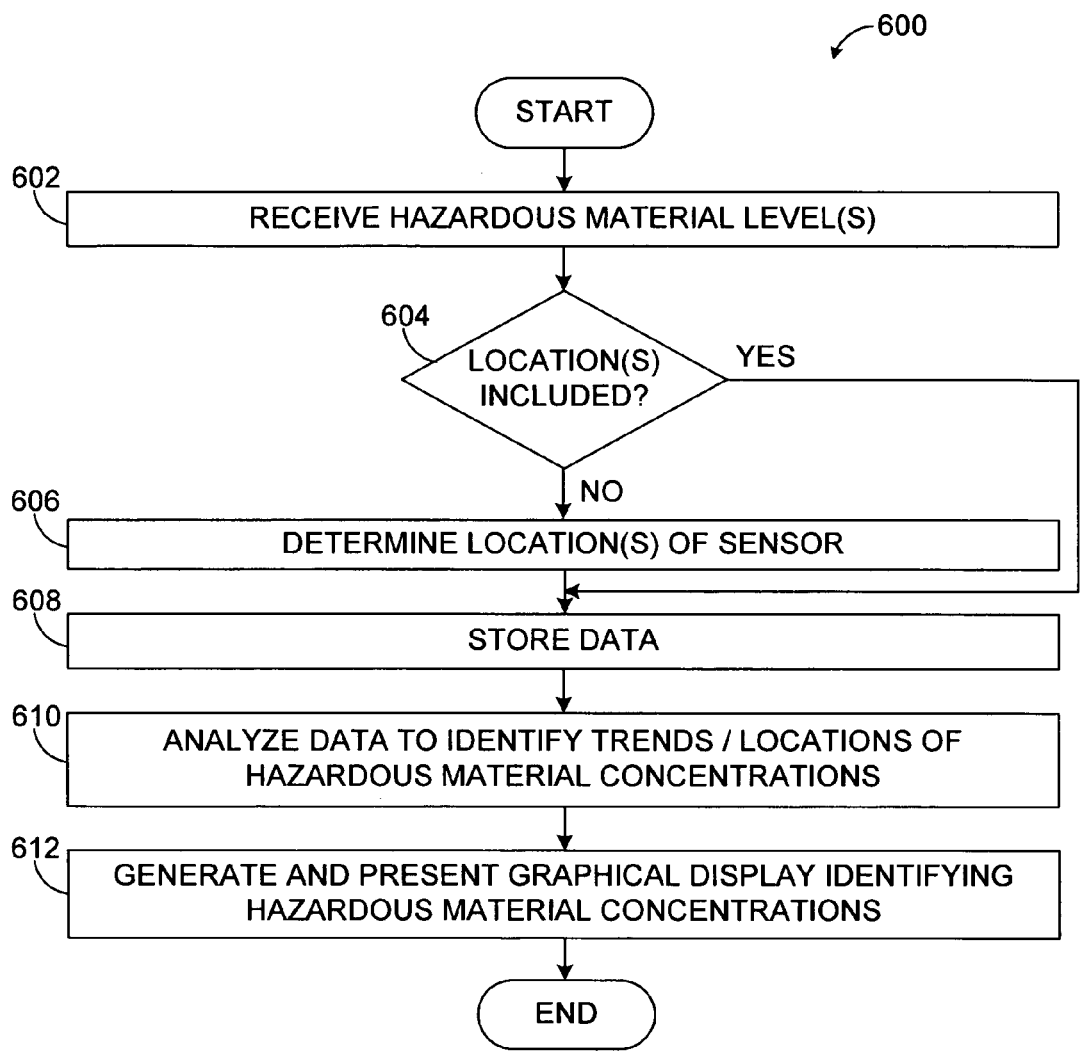
FIG. 6 illustrates an example method for collecting measurements from a hazardous material sensor according to one embodiment of this disclosure.

FIG. 6 illustrates an example method 600 for collecting measurements from a hazardous material sensor according to one embodiment of this disclosure. The embodiment of the method 600 shown in FIG. 6 is for illustration only. Other embodiments of the method 600 may be used without departing from the scope of this disclosure. Also, for ease of explanation, the method 600 is described with respect to the hazardous material sensor 100 of FIG. 1 operating in the systems of FIGS. 2 and 3. The method 600 could be used with any other suitable device and in any other suitable system.

Hazardous material measurement data is received at step 602. This may include, for example, the server 208 receiving the data from a hazardous material sensor 100 via a host 202 or via a transceiver 302a-302n.

A determination is made as to whether the location of the hazardous material sensor 100 is included or associated with the received data at step 604. The location data could represent the location of the hazardous material sensor 100 as determined by the hazardous material sensor 100 or by a transceiver 302a-302n. If not, the location of the hazardous material sensor 100 is determined at step 606. This could include the server 208 using the identity of the transceiver 302a-302n receiving the measurement data from the hazardous material sensor 100, allowing the server 208 to approximate the location of the hazardous material sensor 100.

The data is stored at step 608. This could include storing the data in a database 210. The storage could occur in any suitable manner. For example, the measurement and location data could be stored separately or together.

The data is analyzed at step 610. This could include an application 216 analyzing the data to identify the locations where hazardous materials are or may become excessive. This could also include the application 216 identifying movement of the hazardous materials or any other analysis that uses the hazardous material measurements and the location data.

At this point, the results of the analysis could be used in any suitable manner. For example, a graphical display could be generated and presented at step 612. The graphical display could include a map of a processing or other environment and an identification of hazardous material concentrations in the environment. The graphical display could also identify any warnings specifying where hazardous material concentrations exceed certain thresholds. The analysis results could be used in any other or additional manner.

Although FIG. 6 illustrates one example of a method 600 for collecting measurements from a hazardous material sensor, various changes may be made to FIG. 6. For example, while shown as a series of steps, the method 600 could include steps that overlap or that occur in parallel. Also, the data associated with operation of one or more hazardous material sensors 100 could be used in any other or additional manner.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A portable apparatus, comprising:
a sensor operable to measure one or more hazardous materials;
a memory operable to store measured amounts of the one or more hazardous materials generated by the sensor;
a tracking system operable to identify a location of the apparatus through information provided by the tracking system using at least one beacon broadcast in an industrial processing facility as the apparatus is moved within the industrial processing facility, wherein the sensor and the tracking system are configured to provide information to an external system operable to track trends related to how one or more hazardous materials move in the industrial processing facility;
an interface operable to transmit data from the sensor, the data associated with the measured amounts of the one or more hazardous materials;
a control operable, when manually operated, to trigger measurement of the one or more hazardous materials by the sensor;
a display operable to present information to a user, the information comprising: the measured amounts of the one or more hazardous materials, one or more units of measurement for the measured amounts of the one or more hazardous materials, and an identification of any upper and lower thresholds violated by the measured amounts of the one or more hazardous materials;
a controller configured to trigger an alarm in response to any thresholds violated by the measured amounts of the one or more hazardous materials; and
a waterproof housing containing the sensor, the tracking system, the interface, the control, the display, and the controller, wherein the housing comprises an attachment operable to couple the housing to a moveable object.

2. The apparatus of claim 1, wherein:
the sensor is operable to measure a concentration of the one or more hazardous materials; and
the interface is operable to transmit one or more measured concentrations generated by the sensor.

3. The apparatus of claim 2, wherein:
the tracking system is operable to determine the location of the apparatus; and
the interface is operable to transmit the one or more measured concentrations and one or more determined locations.

4. The apparatus of claim 3, wherein the tracking system is operable to determine the location of the apparatus using at least one of: Global Positioning System (GPS) signals and signals from one or more radio frequency transmitters.

5. The apparatus of claim 2, wherein the tracking system is operable to initiate transmission of signals used by an external system to identify the location of the apparatus.

6. The apparatus of claim 1, wherein the controller is further operable to control operation of at least one of: the sensor, the tracking system, and the interface.

7. The apparatus of claim 6, wherein the controller and the tracking system are operable to cooperate to identify the location of the apparatus.

8. The apparatus of claim 1, wherein the moveable object comprises a conveyor belt.

9. The apparatus of claim 1, wherein:
the sensor is operable to measure a concentration of the one or more hazardous materials;
the controller is operable to determine if the concentration of each hazardous material exceeds a specified threshold associated with that hazardous material; and
the controller is operable to trigger the alarm to provide an indication to the user when the concentration of at least one hazardous material exceeds its associated threshold.

10. The apparatus of claim 9, wherein:
the sensor is operable to measure the concentration of each of multiple hazardous gasses;
the controller is operable to determine if the concentration of each hazardous gas exceeds a lower threshold or an upper threshold; and
the controller is operable to trigger the alarm to provide different indications to the user, the indications varying based on whether the concentration of at least one hazardous gas exceeds its lower threshold or its upper threshold.

11. A method, comprising:
measuring one or more hazardous materials at a portable sensor multiple times, wherein at least one measurement is taken in response to manual operation of a control on the portable sensor;
storing measured amounts of the one or more hazardous materials generated in a memory of the portable sensor;
identifying locations of the portable sensor in a mine as the portable sensor is moved within the mine using information provided by an external system with at least one beacon broadcast, the locations identified at the portable sensor;
transmitting data associated with the measured amounts of the one or more hazardous materials and the identified locations of the sensor to the external system;
displaying information to a user on the portable sensor, the information comprising: the measured amounts of the one or more hazardous materials, one or more units of measurement for the measured amounts of the one or more hazardous materials, and an identification of any thresholds violated by the measured amounts of the one or more hazardous materials;
tracking a movement, a trend and a build-up of the one or more hazardous materials;
triggering an alarm on the portable sensor in response to at least one threshold being violated by the measured amounts of the one or more hazardous materials; and
attaching a waterproof housing of the portable sensor to a moveable object.

12. The method of claim 11, wherein measuring the one or more hazardous materials comprises measuring a concentration of the one or more hazardous materials.

13. The method of claim 12, further comprising:
comparing a measured concentration and the at least one threshold; and
initiating the alarm if the measured concentration exceeds any of the at least one threshold.

14. The method of claim 11, wherein identifying the location of the portable sensor comprises determining the location of the portable sensor signals from one or more radio frequency transmitters.

15. The method of claim 11, wherein transmitting the data and the identified location comprises one of:
downloading the data and the identified location to a host computer; and
transmitting the data and the identified location wirelessly to a radio frequency (RE) receiver.

16. A computer readable medium embodying a computer program, the computer program comprising:
computer readable program code for receiving measurement data associated with one or more hazardous materials from a portable sensor, the sensor associated with an environment, the environment comprising an industrial processing facility, the measurement data comprising measured amounts of the one or more hazardous materials;
computer readable program code for receiving location data identifying locations of the portable sensor in the industrial processing facility as the portable sensor is moved within the industrial processing facility, where the location data is received using at least one broadcast from a beacon;
computer readable program code for analyzing the measurement data and the location data and for tracking trends related to how the one or more hazardous materials move in the environment; and
computer readable program code for presenting a map of the industrial processing facility, an identification on the map of the measured amounts of the one or more hazardous materials, any warnings specifying where the measured amounts of the one or more hazardous materials exceed at least one threshold, an identification on the map of how the one or more hazardous materials move within the industrial processing facility, and an identification on the map of the trends of the one or more hazardous materials.

17. The computer readable medium of claim 16, wherein the map identifies one or more of: locations where a concentration of the one or more hazardous materials exceeds at least one threshold, and a trend in the concentration of the one or more hazardous materials.

18. The computer readable medium of claim 16, wherein:
the sensor is operable to generate the location data identifying the locations of the sensor; and
the computer program comprises computer readable program code for receiving the location data identifying the locations of the sensor from the sensor.

19. The computer readable medium of claim 18, wherein the location data identifying the locations of the sensor is received from the sensor through at least one of: a receiver operable to wirelessly receive the location data in real-time from the sensor and a host computer operable to receive the location data in non-real-time from the sensor.

20. The computer readable medium of claim 16, wherein:
the sensor is operable to transmit signals to one or more receivers; and
the computer program comprises computer readable program code for determining the location data identifying the locations of the sensor using an identity of the one or more receivers that receive the signals transmitted by the sensor.

* * * * *